United States Patent [19]
Connor

[11] Patent Number: 6,166,262
[45] Date of Patent: Dec. 26, 2000

[54] SURFACTANT MANUFACTURE

[75] Inventor: Daniel Stedman Connor, Cincinnati, Ohio

[73] Assignee: The Procter & Gamble Company, Cincinnati, Ohio

[21] Appl. No.: 09/170,711

[22] Filed: Oct. 13, 1998

Related U.S. Application Data

[63] Continuation of application No. PCT/US97/06339, Apr. 16, 1997.
[60] Provisional application No. 60/015,523, Apr. 16, 1996.

[51] Int. Cl.$^7$ .............................. C07C 1/04; C07C 45/00; C07C 305/00
[52] U.S. Cl. .......................... 568/460; 568/451; 585/520; 252/188.2; 252/302; 526/287
[58] Field of Search ..................................... 568/451, 460, 568/28; 585/520; 252/188.2

[56] References Cited

U.S. PATENT DOCUMENTS

| | | | |
|---|---|---|---|
| 2,695,327 | 11/1954 | Ziegler et al. ...................... | 260/683.15 |
| 3,480,556 | 11/1969 | DeWitt et al. .......................... | 252/152 |
| 3,635,829 | 1/1972 | Yang . | |
| 3,647,906 | 3/1972 | Farley ..................................... | 260/683 |
| 3,887,624 | 6/1975 | Gibson et al. ........................ | 260/615 B |
| 4,102,823 | 7/1978 | Matheson .............................. | 252/533 |
| 4,732,707 | 3/1988 | Naik et al. .............................. | 252/548 |
| 4,870,038 | 9/1989 | Page et al. ................................. | 502/62 |
| 5,026,933 | 6/1991 | Blain et al. ................................. | 585/7 |
| 5,245,072 | 9/1993 | Giacobbe et al. .......................... | 560/99 |
| 5,284,989 | 2/1994 | Apelian et al. .......................... | 585/533 |
| 5,446,213 | 8/1995 | Sato et al. ................................ | 568/883 |
| 5,562,866 | 10/1996 | Hu et al. .................................. | 510/432 |
| 5,780,694 | 7/1998 | Singleton ................................ | 568/909 |

FOREIGN PATENT DOCUMENTS

| | | |
|---|---|---|
| 0342917 | 11/1989 | European Pat. Off. . |
| 0401642 | 12/1990 | European Pat. Off. . |
| 0439316 | 7/1991 | European Pat. Off. . |
| 0569773 | 11/1993 | European Pat. Off. . |
| 0684300 | 11/1995 | European Pat. Off. . |
| 1151630 | 2/1958 | France . |
| 2176794 | 11/1973 | France . |
| 2267369 | 7/1975 | France . |
| 2424316 | 11/1979 | France . |
| 2243307 | 9/1972 | Germany . |
| 719445 | 12/1954 | United Kingdom . |
| 1399966 | 7/1975 | United Kingdom . |
| WO 85/02175 | 5/1985 | WIPO . |
| WO 94/11488 | 5/1994 | WIPO . |
| WO 96/18711 | 6/1996 | WIPO . |
| WO 97/01521 | 1/1997 | WIPO . |
| WO 97/38956 | 10/1997 | WIPO . |
| WO 97/38957 | 10/1997 | WIPO . |
| WO 97/38972 | 10/1997 | WIPO . |
| WO 97/39087 | 10/1997 | WIPO . |
| WO 97/39088 | 10/1997 | WIPO . |
| WO 97/39089 | 10/1997 | WIPO . |
| WO 97/39090 | 10/1997 | WIPO . |
| WO 97/39091 | 10/1997 | WIPO . |
| WO 98/23566 | 6/1998 | WIPO . |
| WO 98/23712 | 6/1998 | WIPO . |
| WO 98/35553 | 8/1998 | WIPO . |

OTHER PUBLICATIONS

R. G. Laughlin, "The Aqueous Phase Behavior of Surfactants", *Academic Press*, N.Y. (1980), p. 347.

Finger, et al., "Detergent Alcohols—the effect of alcohol structure and molecular weight on surfactant properties", *J. Amer. Oil Chemists' Society*, vol. 44, (1967), p. 525.

Technical Bulletin, Shell Chemical Company, SC:364–80.

K. R. Wormuth, et al., "Phase Behavior of Branched Surfactants in Oil and Water", *Langmuir*, vol. 7, (1991), pp. 2048–2053.

R. Varadaraj, et al., "Fundamental Interfacial Properties of Alkyl–Branched Sulfate and Ethoxy Sulfate Surfactants Derived from Guerbet Alcohols. 1. Surface and Instantaneous Interfacial Tensions", *J. Phys. Chem.*, vol. 95 (1991), pp. 1671–1676.

R. Varadaraj, et al., "Relationship between Fundamental Interfacial Properties and Foaming in Linear and Branched Sulfate, Ethoxysulfate, and Ethoxylate Surfactants", *Journal of Colloid and Interface Science*, vol. 140, No. 1 (Nov. 1990), pp. 31–34.

R. Varadaraj, et al., "Micropolarity and Water Penetration in Micellar Aggregates of Linear and Branched Hydrocarbon Surfactants", *Langmuir*, vol. 6 (1990), pp. 1376–1378.

R. Varadaraj, et al., "Relationship between Dynamic Contact Angle and Dynamic Surface Tension Properties for Linear and Branched Ethoxylate, Ethoxysulfate, and Sulfate Surfactants", *Journal of Colloid and Interface Science*, vol. 147, No. 2 (Dec. 1991), pp. 403–406.

R. D. Swisher, "Surfactant Biodegradation", *Surfactant Science Series*, $2^{nd}$ Ed., Marcel Dekker, Inc., vol. 18, pp. 20–29 and 34–36.

CEH Marketing Research Report "Detergent Alcohols" by R. F. Modler, et al., *Chemical Economics Handbook*, (1993), pp. 609.5000–609.5002.

"Alcohols, Higher Aliphatic", *Kirk Othmer's Encyclopedia of Chemical Technology*, $4^{th}$ Ed., Wiley, N.Y., (1991), vol. 1, pp. 865–913.

"Liquid Fuels", *Kirk Othmer's Encyclopedia of Chemical Technology*, Wiley, N.Y., (1989), vol. 11, pp. 447–489.

"Oxo Process", *Kirk Othmer's Encyclopedia of Chemical Technology*, Wiley, N.Y., (1989), vol. 16, pp. 637–653.

"Sasol Detergent Alcohols", R&D Technical Bulletin, Sasol Alpha Olefins, (Oct. 1, 1996), pp. 1–12.

*Primary Examiner*—Tae Yoon
*Attorney, Agent, or Firm*—Ian S. Robinson; Kim William Zerby; Steven W. Miller

[57] ABSTRACT

Branched-chain olefins are prepared and used as feedstocks in the manufacture of detersive surfactants.

10 Claims, No Drawings

SURFACTANT MANUFACTURE

CROSS REFERENCE

This is a continuation of PCT International Application Serial No. PCT/US97/06339, filed Apr. 16, 1997; which claims priority to Provisional Application Serial No. 60/015,523, filed Apr. 16, 1996.

FIELD OF THE INVENTION

The present invention relates to processes for manufacturing detersive surfactants, especially those containing branched-chain hydrophobic units.

BACKGROUND OF THE INVENTION

Conventional detersive surfactants comprise molecules having a water-solubilizing substituent (hydrophilic group) and an oleophilic substituent (hydrophobic group). Such surfactants typically comprise hydrophilic groups such as carboxylate, sulfate, sulfonate, amine oxide, polyoxyethylene, and the like, attached to an alkyl, alkenyl or alkaryl hydrophobe usually containing from about 10 to about 20 carbon atoms. Accordingly, the manufacturer of such surfactants must have access to a source of hydrophobe groups to which the desired hydrophile can be attached by chemical means. The earliest source of hydrophobe groups comprised the natural fats and oils, which were converted into soaps (i.e., carboxylate hydrophile) by saponification with base. Coconut oil and palm oil are still used to manufacture soap, as well as to manufacture the alkyl sulfate ("AS") class of surfactants. Other hydrophobes are available from petrochemicals, including alkylated benzene which is used to manufacture alkyl benzene sulfonate surfactants ("LAS").

The literature asserts that certain branched hydrophobes can be used to advantage in the manufacture of alkyl sulfate detersive surfactants; see, for example, U.S. Pat. No. 3,480,556 to deWitt, et al., Nov. 25, 1969. However, it has been determined that the beta-branched surfactants described in the '556 patent are inferior with respect to certain solubility parameters, as evidenced by their Krafft temperatures. It has further been determined that surfactants having branching towards the center of carbon chain of the hydrophobe have much lower Krafft temperatures. See: "The Aqueous Phase Behavior of Surfactants", R. G. Laughlin, Academic Press, N.Y. (1994) p. 347. Accordingly, it has now been determined that such surfactants are preferred for use especially under cool or cold water washing conditions (e.g., 20° C.–5° C.).

One problem associated with the manufacture of detersive surfactants having hydrophobe groups with mid- or near-mid chain branching is the lack of a ready source of such hydrophobes. By the present invention, a process is described for manufacturing such branched hydrophobes and converting them into mid- or near-mid chain branched surfactants.

SUMMARY OF THE INVENTION

The present invention encompasses a process for preparing mid- to near mid-chain branched olefins (primarily, methyl branched at or near the mid-chain region). Such materials are then used as the basic feedstock which provides the hydrophobic portion of branched-chain detersive surfactants.

The process herein is designed to provide branched reaction products which are primarily (85%, or greater) alpha-olefins, and which are then converted into hydrophobes in the Oxo-reaction sequence noted hereinafter. Preferably, such branched alpha-olefins contain from about 11 to about 18 (avg.) total carbon atoms and comprise a linear chain having an average length in the 10–18 region. The branching is predominantly mono-methyl, but some di-methyl and some ethyl branching may occur. Advantageously, the present process results in little (1%, or less) geminal branching, i.e., little, if any, "quaternary" carbon substitution. Moreover, little (less than about 20%) vicinal branching occurs. Of course, some (ca. 20%) of the overall feedstock used in the subsequent Oxo-process may remain unbranched. Typically, and preferably from the standpoint of cleaning performance and biodegradability, the present process provides alpha-olefins with: an average number of branches (longest chain basis) in the 0.4–2.5 range; of the branched material, there are essentially no branches on carbons 1, 2 or on the terminal (omega) carbon of the longest chain of the branched material.

Following the formation and purification of the branched-chain alpha-olefin, the feedstock is subjected to an Oxo carbonylation process. In this Oxo-step, a catalyst (e.g., conventional cobalt carbonyl; see Kirk Othmer, below) which does not move the double bond from its initial position is used. This avoids the formation of vinylidene intermediates (which ultimately yield less favorable surfactants) and allows the carbonylation to proceed at the #1 and #2 carbon atoms.

All percentages, ratios and proportions herein are by weight, unless otherwise specified. All documents cited herein are, in relevant part, incorporated herein by reference.

DETAILED DESCRIPTION OF THE INVENTION

As can be seen from the foregoing, the present invention thus encompasses, in a process for preparing surfactant precursor hydrophobes from hydrocarbon feedstocks by the conversion of a coal or other hydrocarbon source to a mixture of carbon monoxide and hydrogen and the subsequent conversion of the carbon monoxide and hydrogen into a mixture of linear and branched hydrocarbons, the improvement which comprises abstracting from said mixture of linear and branched hydrocarbons the sub-set of branched hydrocarbons of the general formula:

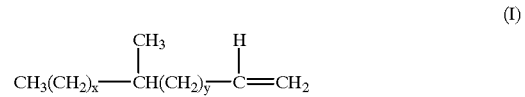

(I)

wherein x is at least about 2, y is greater than or equal to 0 and wherein the sum of x+y is at least about 7.

The invention also encompasses, in a process for preparing surfactant precursor hydrophobes from coal or other hydrocarbon feedstocks by the conversion of such feedstocks to a mixture of carbon monoxide and hydrogen and the subsequent conversion of the carbon monoxide and hydrogen into a mixture of linear and branched hydrocarbons, the improvement which comprises abstracting from said mixture of linear and branched hydrocarbons the sub-set of branched hydrocarbons of the general formula:

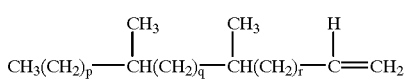

wherein p is at least about 2, q is 1 to 12, r is greater than or equal to 0 and the sum of p, q and r is at least about 6.

The invention also encompasses, in a process for preparing surfactant precursor hydrophobes from coal or other hydrocarbon feedstocks by the conversion of such feedstocks to a mixture of carbon monoxide and hydrogen and the subsequent conversion of the carbon monoxide and hydrogen into a mixture of linear and branched hydrocarbons, the improvement which comprises abstracting from said mixture of linear and branched hydrocarbons the set of branched hydrocarbons comprising a mixture of:

(a) the sub-set of mono-methyl branched compounds of the formula:

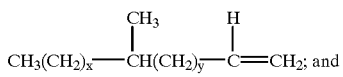

(b) the sub-set of di-methyl branched compounds of the formula:

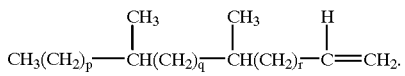

The foregoing branched hydrophobes can then be converted into the corresponding branched-chain detersive surfactants, in the manner disclosed hereinafter.

Process

Synthesis gas (carbon monoxide/hydrogen) can be produced from coal or other hydrocarbon feedstocks such as natural gas and used to build-up various saturated and unsaturated linear, branched and cyclic hydrocarbons using conventional Fischer-Tropsch (F-T) chemistry. Such processes can be used to make a range of hydrocarbons to meet the gasoline, diesel and jet fuel needs. Two points with regard to the present invention are: first, recognition that branching occurs in F-T chemistry through free radical, not carbonium ion chemistry. This leads to isolated methyl branches with no gem-dimethyl, little ethyl and low levels of vicinal-dimethyl branches. Low pressure/low temp (i.e. wax producing) F-T chemistry builds up methylenes mostly in a linear fashion with typically about 1 methyl branch per 50 carbons. At higher pressures and/or higher temperatures (such as used for gasoline production) 1 methyl branch per 8 carbon atoms can be achieved. The rearrangement to form the methyl branch, which occurs adjacent to catalyst, can be thought of a hydrogen atom shift from the beta methylene to the alpha methylene converting it to the methyl branch. Catalyst (Fe, Co, Ru, etc.) moves from alpha to beta and with insertion of additional methylene(s) between catalyst and the methine group (former beta), isolation of the methyl branch is complete. The second key point is that alpha olefins can be a major product of F-T chemistry.

The present invention makes use of such observations to provide an overall method for preparing mid- or near-mid chain branched alpha-olefins which can be converted to the corresponding detersive surfactants, either directly or through the formation of intermediate compounds (e.g., branched-chain alcohols) which are subsequently converted into surfactants. Importantly, the surfactants thus made contain little or no contaminants such as the geminal or vicinal branches or multiple chain branches (i.e., more than about 3 branches). On a weight basis, such contaminants can detract from overall detergency performance and/or biodegradability of the final surfactant products herein.

The overall process herein is as follows:

The Fischer-Tropsch process is described in *Kirk-Othmer Encyclopedia of Chemical Technology,* 4th Edition, Volume 12, pp. 157–164 (1994), Jacqueline I. Kroschwitz, Executive Editor, Wiley-Interscience, N.Y. The Oxo process to make alcohols is described in detail in *Kirk-Othmer Encyclopedia of Chemical Technology,* 4th Edition, Volume 1, pp. 903–8 (1991).

1) Synthesis gas, a mixture of carbon monoxide/hydrogen is typically generated from coal or natural gas, however petroleum or other hydrocarbon sources could in principle be utilized. Air or oxygen is used to partially burn gas, petroleum, etc., to a mixture of carbon monoxide and hydrogen. Similarly, coal or coke can undergo the coke-water-gas reaction to form carbon monoxide and $H_2$. The water gas shift reaction can be used to change the carbon monoxide/hydrogen ratio as required. Various standard cleanup steps are included to remove carbon dioxide, hydrogen sulfide, ammonia etc.

Gas+air or $O_2 \rightarrow CO/H_2$ mixture $C+H_2O \rightarrow CO+H_2$ coke-water-gas reaction $CO+H_2O \rightarrow H_2+CO_2$ (water gas shift)

2) Fischer-Tropsch (F-T) chemistry is used to convert synthesis gas into a mostly hydrocarbon mixture. Conditions can be set to produce a mostly linear olefin mixture with a limited number of methyl branches as well as some cyclic hydrocarbons. Small amounts of other classes of compounds such as alcohols are also formed. Their levels can be somewhat controlled by F-T conditions; in any event they can be removed.

$CO/H_2 \rightarrow$ Syn Fuel Mixture+Branched Alpha-Olefins

3) Distillation and other standard techniques are used to isolate the desired MW hydrocarbon fraction containing alpha-olefins. Molecular sieving can be used to separate most of the linear alpha-olefins and cyclics from the desired, limited methyl-branched, linear alpha-olefins. Standard methods utilizing zeolites can accomplish the former. Processing with zeolite sieves can be arranged to remove iso and anteiso (omega-1) and (omega-2) methyl alpha olefins, if so desired. Aliphatic hydrocarbons containing 2 geminal Me groups or highly branched aliphatic hydrocarbons (including cyclics) can be separated from aliphatic hydrocarbons containing Me groups on different C atoms and less branched aliphatic hydrocarbons by selective adsorption of the latter on a molecular sieve (pore diam. 4.4–5.0 A°) and/or from pyrolyzed poly(vinylidene chloride) (Saran) to yield gasoline with improved octane numbers; see Neth Appl. 7111508 Oct. 25, 1971, *Chem. Abstracts* 76:88253.

Syn Fuel Mixture→Branched alpha-Olefins

4) Oxo chemistry (CO/$H_2$) is used to convert the branched alpha-olefin to the corresponding branched primary alcohol. Any Oxo catalyst which leads directly to alcohols or indirectly through an additional step of hydrogenation of intermediate aldehyde can be used. However it is preferable to use catalysts which do not isomerize the double bond of the alpha-olefin prior to carbonylation as is the case using cobalt-carbon monoxide-organophosphine catalysts in the one step process. Conventional cobalt Oxo catalysts such as cobalt-carbon monoxide used in the two step high pressure process do not isomerize the C=C double bond. The fact these can give approximately equal carbonylation on 1- and 2-carbon positions of the alpha olefin is entirely acceptable. In other words the product mixture would be $RCH_2CH_2CH_2OH+RCH(CH_3)CH_2OH$ where R is linear fatty chain with limited methyl branching at the mid- or near-mid chain region.

Branched Alpha-olefins→Branched Primary Alcohols

5) In one aspect of the last step, any standard sulfation technique may be used to convert the above branched alcohol to a branched alcohol sulfate. Examples are sulfur trioxide in a falling film reactor or sulfur trioxide or chlorosulfonic acid in a batch reactor. In any case the acid mixture is promptly neutralized with caustic soda, or the like.

Branched Primary Alcohol→Branched Alkyl Sulfate

Other fatty alcohol-derived surfactants can also be made, e.g., alkyl ethoxy sulfates (AES), alkyl polyglucosides (APG), etc. Note that surfactants other than alcohol sulfates or AES may be made by oxidizing said alcohol or its aldehyde intermediate into a carboxylate (i.e., a branched-chain soap). This soap can be an excellent surfactant and/or detergent builder in and of itself. This carboxylate can also be used as a feedstock and converted to branched acyl-aurates, -isethionates, -sarcosinates, -N-methylglucamides or other similar acyl-derived surfactants, using art-disclosed techniques.

INDUSTRIAL APPLICABILITY

Branched-chain surfactants of the type resulting from the present process can be used in all manner of cleaning compositions. Such compositions include, but are not limited to: granular, bar-form and liquid laundry detergents; liquid hand dishwashing compositions; liquid, gel and bar-form personal cleansing products; shampoos; dentifrices; hard surface cleaners, and the like. Such compositions can contain a variety of conventional detersive ingredients. The following listing of such ingredients is for the convenience of the formulator, and not by way of imitation of the types of ingredients which can be used with the branched-chain surfactants herein.

The branched-chain surfactants herein can be used in combination with detergency builders. Such builders include, for example, 1–10 micrometer zeolite A, polycarboxylate builders such as citrate, layered silicate builders such as "SKS-6" (Hoechst) and phosphate materials, especially sodium tripolyphosphate ("STPP"). Most laundry detergents typically comprise at least about 1% builder, more typically from about 5% to about 80% builder or mixtures of builders.

Enzymes, such as proteases, amylases, lipases, cellulases, peroxidases, and mixtures thereof, can be employed in detergent compositions containing the branched-chain surfactants. Typical detergent compositions comprise from about 0.001% to about 5% of commercial enzymes.

Detergent compositions can also contain polymeric soil release agents (SRA's). Such materials include, for example, anionic, cationic and non-charged monomer units, especially polyester materials. Preferred materials of this type include oligomeric terephthalate esters, sulfonated substantially linear ester oligomers comprising a backbone of terephthaloyl and oxyalkyleneoxy repeat units and phthalolyl-derived sulfonated terminal moieties. A variety of SRA's are described, for example, in U.S. Pat. Nos. 4,968, 451; 4,711,730; 4,721,580; 4,702,857; 4,877,896; 5,415,807; and in other literature references. Such soil release materials typically comprise from about 0.01% to about 10% of finished detergent compositions.

Detergent compositions may also optionally contain bleaching compositions comprising a bleaching agent and one or more bleach activators. If present, bleaching agents such as percarbonate or perborate (especially perborate monohydrate "PB1") typically are used at levels from about 1% to about 30% of finished detergent compositions. Bleach activators such as nonanoyloxy-benzene sulfonate ("NOBS") and tetraacetyl ethylenediamine ("TAED"), and mixtures thereof, can be used to enhance the bleaching activity of materials such as perborate and percarbonate. If present, the amount of bleach activator will typically be from about 0.1% to about 60% of a bleaching composition comprising a bleaching agent-plus-bleach activator. Other bleaching agents such as the so-called "photoactivated" bleaches (see U.S. Pat. No. 4,033,718) can also be used. Sulfonated zinc phthalocyanine is an especially preferred photoactivated bleaching agent.

Detergent compositions can also contain clay soil removal/antiredeposition agents such as ethoxylated tetraethylene pentamine; see U.S. Pat. No. 4,597,898. Such materials typically comprise from about 0.01% to about 10% of fully-formulated laundry detergents.

Detergent compositions can also contain from about 0.1% to about 7% of polymeric dispersing agents, which are especially useful in the presence of zeolite and/or layered silicate builders. Such materials are known in the art (see U.S. Pat. No. 3,308,067). Such materials include acrylate/malic-based copolymers, such as described in EP 193,360, as well as polyethylene glycol ("PEG").

Detergent compositions herein can also include various brighteners, dye transfer inhibiting agents (especially polymers of N-vinylpyrrolidone and N-vinylimidazole), suds suppressors (especially silicones), chelating agents such as nitrilotriacetate, ethylenediamine disuccinate, and the like. Such materials will typically comprise from about 0.5% to about 10%, by weight, of fully-formulated cleaning compositions.

Moreover, it is to be understood that the branched-chain surfactants prepared in the manner of the present invention may be used singly in cleaning compositions or in combination with other detersive surfactants. Typically, fully-formulated cleaning compositions will contain a mixture of surfactant types in order to obtain broad-scale cleaning performance over a variety of soils and stains and under a variety of usage conditions. One advantage of the branched-chain surfactants herein is their ability to be readily formulated in combination with other known surfactant types. Nonlimiting examples of additional surfactants which may be used herein typically at levels from about 1% to about 55%, by weight, include the unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. Nonionic surfactants such as the ethoxylated $C_{10}$–$C_{18}$ alcohols and alkyl phenols, (e.g., $C_{10}$–$C_{18}$ EO (1–10) can also be used. If desired, other conventional surfactants such as the $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl)

glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. $C_{10}$–$C_{14}$ alkyl benzene sulfonates (LAS), which are often used in laundry detergent compositions, can also be used with the branched surfactants herein.

The following Examples illustrate the use of branched-chain surfactants prepared according to the present invention in various cleaning compositions, but is not intended to be limiting thereof.

EXAMPLE I

Granular laundry detergents are prepared as follows.

|  | A | B | C |
|---|---|---|---|
| Blown Powder |  |  |  |
| Zeolite A | 30.0 | 22.0 | 6.0 |
| Sodium sulfate | 19.0 | 5.0 | 7.0 |
| Polyacrylate |  |  |  |
| LAS | 13.0 | 11.0 | 21.0 |
| Branched AS* | 9.0 | 8.0 | 8.0 |
| Silicate, Na | — | 1.0 | 5.0 |
| Soap | — | — | 2.0 |
| Carbonate, Na | 8.0 | 16.0 | 20.0 |
| Spray On |  |  |  |
| $C_{14-15}$EO7 | 1.0 | 1.0 | 1.0 |
| Dry additives |  |  |  |
| Protease | 1.0 | 1.0 | 1.0 |
| Lipase | 0.4 | 0.4 | 0.4 |
| Amylase | 0.1 | 0.1 | 0.1 |
| Cellulase | 0.1 | 0.1 | 0.1 |
| NOBS | — | 6.1 | 4.5 |
| PB1 | 1.0 | 5.0 | 6.0 |
| Sodium sulfate | — | 6.0 | — |
| Moisture & Miscellaneous |  | Balance |  |

*$C_{12}$-$C_{14}$ methyl branched alkyl sulfate, prepared as disclosed above.

A bleach-containing nonaqueous liquid laundry detergent is prepared as follows.

EXAMPLE II

| Component | Wt. % | Range (% wt.) |
|---|---|---|
| Liquid Phase |  |  |
| Branched AS* | 25.3 | 18–35 |
| $C_{12-14}$, EO5 alcohol ethoxylate | 13.6 | 10–20 |
| Hexylene glycol | 27.3 | 20–30 |
| Perfume | 0.4 | 0–1.0 |
| Solids |  |  |
| Protease enzyme | 0.4 | 0–1.0 |
| $Na_3$ Citrate, anhydrous | 4.3 | 3–6 |
| Sodium perborate (PB-1) | 3.4 | 2–7 |
| Sodium nonanoyloxybenzene sulfonate (NOBS) | 8.0 | 2–12 |
| Sodium carbonate | 13.9 | 5–20 |
| Diethyl triamine pentaacetic acid (DTPA) | 0.9 | 0–1.5 |
| Brightener | 0.4 | 0–0.6 |
| Suds Suppressor | 0.1 | 0–0.3 |
| Minors | Balance |  |

*$C_{12}$-$C_{16}$ methyl branched alkyl sulfate, Na salt, prepared as disclosed above.

A hand dishwashing liquid is as follows.

EXAMPLE III

| Ingredient | % (wt.) | Range (% wt.) |
|---|---|---|
| Branched AS* | 13.0 | 5–15 |
| Ammonium $C_{12-13}$ alkyl ethoxy sulfate | 15.0 | 10–35 |
| Coconut amine oxide | 2.6 | 2–5 |
| Betaine**/Tetronic 704 ® | 0.87–0.10 | 0–2 (mix) |
| Alcohol Ethoxylate $C_8E_{11}$ | 5.0 | 2–10 |
| Ammonium xylene sulfonate | 4.0 | 1–6 |
| Ethanol | 4.0 | 0–7 |
| Ammonium citrate | 0.06 | 0–1.0 |
| Magnesium chloride | 3.3 | 0–4.0 |
| Calcium chloride | 2.5 | 0–4.0 |
| Ammonium sulfate | 0.08 | 0–4.0 |
| Hydrogen peroxide | 200 ppm | 0–300 ppm |
| Perfume | 0.18 | 0–0.5 |
| Maxatase ® protease | 0.50 | 0–1.0 |
| Water and minors | Balance |  |

*$C_{12}C_{14}$ methyl branched alkyl sulfate, triethanolammonium salt, prepared as disclosed above.
**Cocoalkyl betaine.

What is claimed is:

1. A process for preparing mid- to near-mid chain branched alpha olefins, comprising the steps of:

(a) preparing a mixture of CO and $H_2$;

(b) reacting the mixture of CO and $H_2$ in the presence of a catalyst under Fischer-Tropsch conditions to prepare a hydrocarbon mixture comprising said mid- to near-mid chain branched alpha-olefins; and (c) separating said branched alpha-olefins from said hydrocarbon mixture.

2. A process according to claim 1 wherein the catalyst of step (b) is a member selected from the group consisting of Fe, Co and Ru Fischer-Tropsch catalysts.

3. A process according to claim 1 wherein said alpha-olefins are separated using molecular sieves and/or pyrolyzed poly(vinylidene chloride).

4. A process for preparing mid- to near-mid chain branched alcohols, comprising reacting the branched alpha-olefins made in accordance with claim 1 with CO/$H_2$ under Oxo conditions.

5. A process according to claim 4 which is conducted without isomerization of the olefin double bond using a cobalt-carbon monoxide catalyst.

6. A process according to claim 5 which yields alcohols of the formula $RCH_2CH_2CH_2OH$ and $RCH(CH_3)CH_2OH$, wherein R is $C_8$ to $C_{16}$ alkyl with methyl branching.

7. A process for preparing branched alkyl sulfate surfactants, comprising sulfating the alcohols prepared according to claim 4.

8. A process for preparing branched alkyl ethoxy sulfates, comprising first ethoxylating, then sulfating, the alcohols prepared according to claim 4.

9. A process for preparing branched alkyl carboxylate surfactants (soaps) by oxidizing the alcohols prepared according to claim 4, or their aldehyde intermediates.

10. A process for preparing branched acyl taurate, branched acyl isethionates, branched acyl sarcosinate or branched acyl N-methylglucamide surfactants using the branched carboxylates prepared according to claim 9 as a feedstock.

\* \* \* \* \*